United States Patent [19]

Häbig et al.

[11] Patent Number: 4,796,778
[45] Date of Patent: Jan. 10, 1989

[54] LOCKING MECHANISM

[75] Inventors: Klaus Häbig; Wolfgang Taschner, both of Tuttlingen; Wilfried Wölfle, Bad Dürrheim, all of Fed. Rep. of Germany

[73] Assignee: Aesculap-Werke AG vormals Jetter & Scheerer, Fed. Rep. of Germany

[21] Appl. No.: 176,366

[22] Filed: Mar. 21, 1988

[30] Foreign Application Priority Data

Mar. 27, 1987 [DE] Fed. Rep. of Germany ....... 3710049

[51] Int. Cl.⁴ .............................................. B65D 45/00
[52] U.S. Cl. ..................................... 220/315; 220/326
[58] Field of Search ................................ 220/315, 326

[56] References Cited

U.S. PATENT DOCUMENTS 2,936,189 5/1960 Pearson ................................ 220/326
3,080,995 3/1963 Palm ..................................... 220/326

*Primary Examiner*—George T. Hall
*Attorney, Agent, or Firm*—Kramer, Brufsky & Cifelli

[57] ABSTRACT

In a locking mechanism, in particular, for fixing filter holders on sterilizing containers, with a housing in which a locking member is displaceable between two end positions, namely a first end position in which it engages behind a locking projection, and a second end position in which it releases the locking projection, with a spring means which biases the locking member in the direction towards the first end position, and with an actuating member protruding from the housing for displacement of the locking member, in order to ensure that unlocking does not occur if the actuating member is unintentionally actuated, it is suggested that a second actuating member be provided and that the actuating members be arranged on the housing on opposite sides thereof and be actuatable by displacement in the direction towards the respective other actuating member, the locking mechanism only being unlockable if both actuating members are actuated.

15 Claims, 2 Drawing Sheets

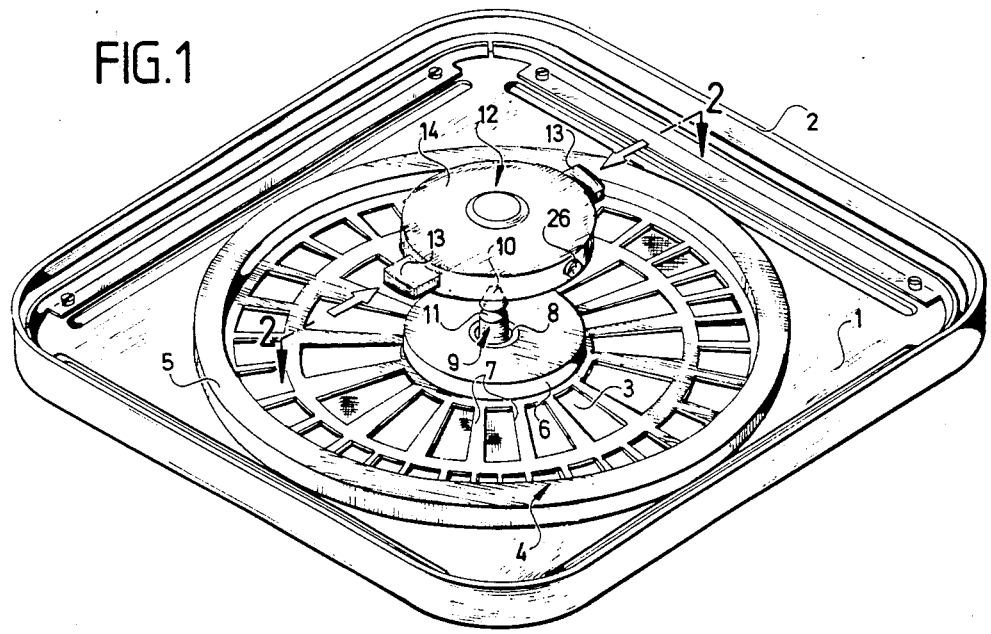
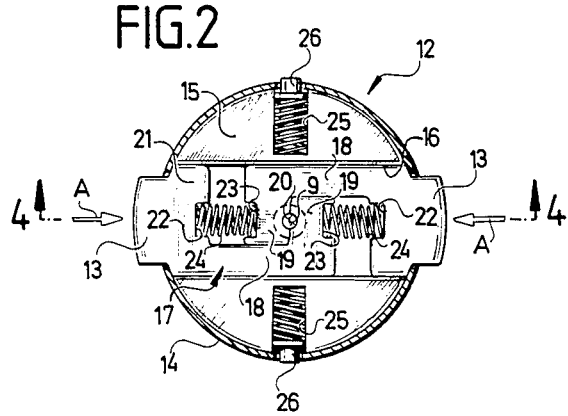
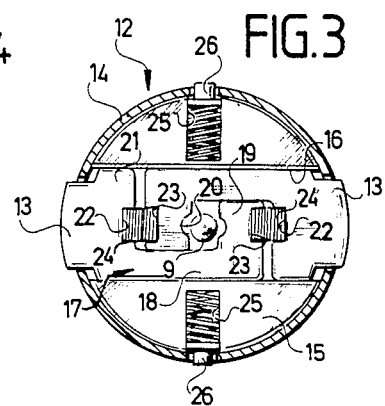
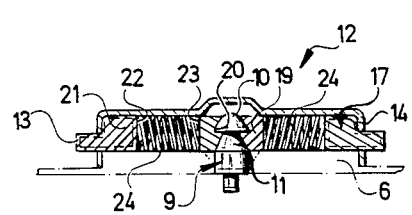

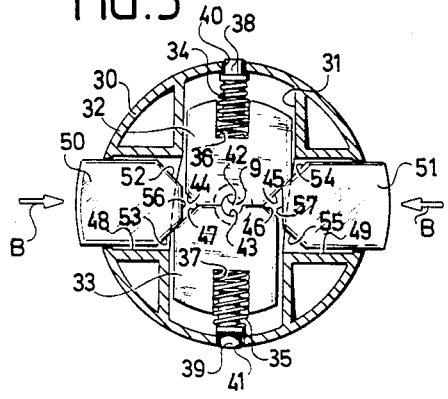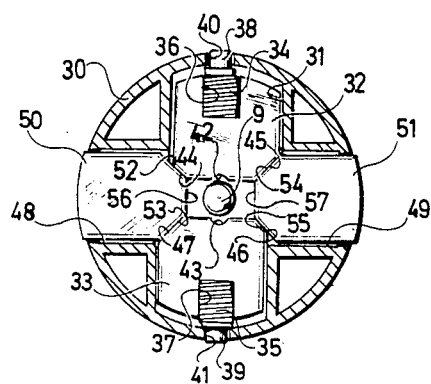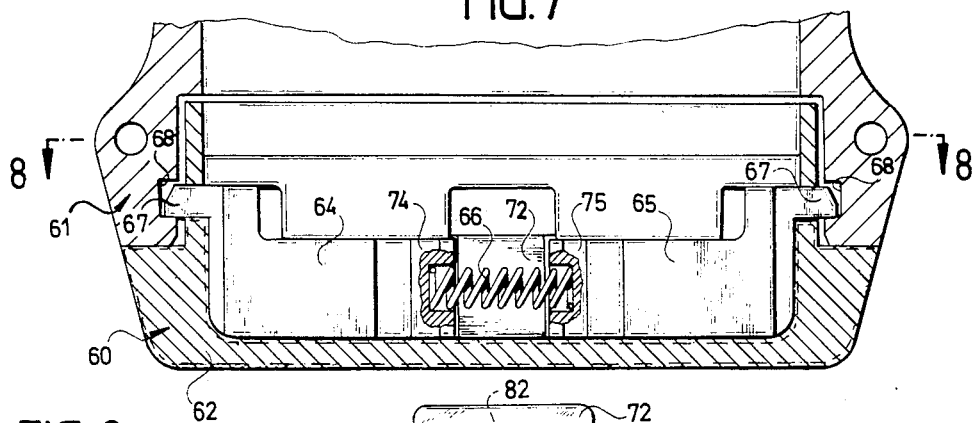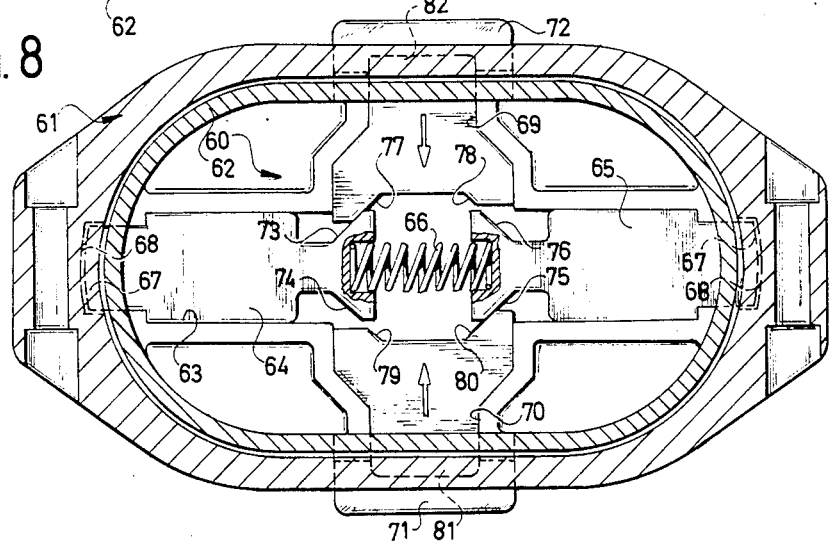

LOCKING MECHANISM

The invention relates to a locking mechanism, in particular, for fixing filter holders on sterilizing containers, with a housing in which a locking member is displaceable between two end positions, namely a first end position in which it engages behind a locking projection and a second end position in which it releases the locking projection, with a spring means which biases the locking member in the direction towards the first end position, and with an actuating member which protrudes from the housing for displacement of the locking member.

In order to releasably fix one part on another, for example, a filter paper holder on the lid of a perforated sterilizing container, locking mechanisms can be used which cause automatic connection of the two parts when applied and which can be removed from their position by actuation of an actuating member, whereby the connection of the previously locked parts is released again.

Such a locking mechanism has, for example, been suggested for fixing on the inside of the perforated container lid of a sterilizing container a filter sheet which covers the perforations in the lid. The filter sheet is pressed by a plateshaped filter holder against the inside of the lid. This holder is fixed by a locking mechanism which is set on a locking pin fixed on the lid such that it engages behind a recess on the locking pin and in this position presses the holder and the filter sheet against the lid. A displaceable locking member which in the fixed position engages behind a detent projection on the locking pin is mounted in the locking mechanism. An actuating member protruding from the housing of the locking mechanism can move the locking member into the open position via a deflector mechanism and the locking mechanism can then be removed from the locking pin. The holder pressing the filter sheet against the inside of the lid is thereby also released.

In order to release the locking in this device, it is, therefore, merely necessary to operate an actuating member and, in particular, if the filter holder is of resilient design, the locking mechanism is then automatically removed from its locking position.

While this simple unlocking is, on the one hand, very advantageous, it may, on the other hand, also be expedient for the locking not to be releasable in such a simple way since this involves the danger of the locking being released when this is not wanted, by the actuating member being unintentionally pressed, for example, by an instrument arranged in the sterilizing container.

With other locking and closure mechanisms, too, it may, in order to prevent inadvertent unlocking, be expedient for locking members not to be released once a displaceable actuating member has been pressed.

The object of the invention is to further develop a locking mechanism of the generic kind such that it cannot be inadvertently unlocked by an actuating member being pressed.

This object is accomplished, in accordance with the invention, with a locking mechanism of the kind described at the beginning by a second actuating member which protrudes from the housing being provided and by the actuating members protruding from the housing on opposite sides thereof and being actuatable by displacement in the direction towards the respective other actuating member, the locking mechanism only being unlockable if both actuating members are actuated.

Provision of a pair of oppositely arranged actuating members enables these to be actuated in a particularly simple way as it is then sufficient to push them towards one another. Nevertheless, unlocking by unintentional actuation of only one actuating member is excluded.

In a first preferred example, provision is made for two locking members to be mounted in the housing and for one of the two actuating members to be associated with each locking member. With such a configuration, actuation of only one actuating member also results in release of one locking member only while the other locking member continues to hold the locking mechanism in the locking position. Only when both locking members are released by the corresponding actuating members, can the locking mechanism as a whole be removed.

In this case, it is particularly advantageous for the actuating members to be connected to the locking members or for the actuating members and the locking members to be of integral construction.

In a particularly preferred embodiment, provision may be made for the locking members to have an arm which extends transversely to the direction of displacement and engages behind a detent pin in the housing when the locking member is in the first end position, and for the arms of the two locking members to rest against each other, in the first end position, and thereby enclose the detent pin. It is then, furthermore, advantageous for a spring to be arranged between the arm of one locking member and the other locking member so as to push the two locking members into the first end position. As a result of this, when only one actuating member is actuated, the other locking member is pushed particularly firmly into the closed position, which reliably ensures that, in this case, the other locking member maintains its closing function.

It is particularly expedient for the two locking members to be of identical design and to be inserted in the housing in point-symmetrical relation to the detent pin.

In a further preferred embodiment, the respective other locking member moves into the path of displacement of the actuating member associated with the one locking member and thereby prevents its displacement so long as the respective other locking member is in the first end position, and prior to obstruction by the respective other locking member, each actuating member can be pushed forward so far that the associated locking member is removed from the path of displacement of the respective other actuating member.

Accordingly, in such a configuration, motion of each actuating member is blocked if the respective locking member not associated with it is still in its first end, i.e., closing position. The blocking does, however, not occur at the beginning of the path of motion of the actuating member. In this way, each actuating member can be displaced to some extent before the blocking occurs, more particularly, to the extent that the associated locking member is then likewise slightly displaced from its first end, i.e., closing position. This slight displacement of the locking member is sufficient for the displacement path of the respective other actuating member to thereby be opened. Therefore, if only one actuating member is actuated, its motion is blocked by the other, unmoved locking member after short displacement, and opening of the locking members is not possible. The same does, of course, apply to the other actuating member. If, on the other hand, both actuating members are simultaneously actuated, both locking members are displaced from the very beginning and so the locking members are removed from the path of displacement of the respective other actuating member and cannot obstruct full actuation of the actuating members.

In an advantageous elaboration, provision is made for the actuating members to be displaceable perpendicularly to the locking members in the housing, the actuating members and the locking members being, in each case, arranged opposite each other. The actuating members and the associated locking members may then have contiguous wedge surfaces for transmitting the displacement motion from the actuating members to the locking members.

It is, furthermore, advantageous for the actuating members and the locking members which are not associated therewith to have additional wedge surfaces and for the additional wedge surface of an actuating member to rest against the additional wedge surface of the other locking member when the actuating member is displaced. In this way, the actuating members actuate not only the associated locking members, but after a short displacement path also the respective other locking members. This special arrangement results in forces being applied symmetrically to the actuating members and locking members, whereas at the beginning of the displacement, displacement forces are applied to the actuating members and the associated locking members on one side only.

In a particularly preferred embodiment of the invention, provision is made for the locking mechanism to be designed as lid of a container, in particular, a battery container, and for the container to have locking projections. A battery container lid of such design cannot be opened if an actuating member is inadvertently pushed. Opening is only possible if both actuating members are simultaneously actuated.

It is particularly advantageous for the actuating members to have claws which engage behind the projections on the container so long as the actuating members are not pushed in, but release these projections once the actuating members are pushed in. In this way, not only the locking members act as locking mechanisms but also the claws of the actuating members and, therefore, the lid is locked at four points on the container. This locking can only be released if both actuating members are simultaneously pushed in.

The following description of preferred embodiments serves in conjunction with the appended drawings to explain the invention in greater detail. In the drawings:

FIG. 1 is a perspective view of the inside of a lid of a sterilizing container with a filter holder and an inventive locking mechanism;

FIG. 2 is a sectional view of the locking mechanism along line 2—2 in FIG. 1, with the locking members in their closed position;

FIG. 3 is a view similar to FIG. 2 with the locking members in their open position;

FIG. 4 is a sectional view of the locking mechanism along line 4—4 in FIG. 2;

FIG. 5 is a sectional view corresponding to the illustration in FIG. 2 of a modified embodiment of a locking mechanism with closed locking members;

FIG. 6 is a view similar to FIG. 5 with open locking members;

FIG. 7 is a sectional view of part of a battery container with a locking mechanism designed as lid; and FIG. 8 is a sectional view of the container illustrated in FIG. 7 along line 8—8 in FIG. 7.

The locking mechanism illustrated in the drawings can be used in various ways, in some instances as device for fixing one part to another part, and in other instances as device which itself is fixed to another part and, for example, seals an opening in this other part.

The structure of the inventive locking mechanism is described below for both types, namely with reference to one example in which it fixes a filter sheet holder to the lid of a sterilizing container and with reference to another example in which it serves as lid element for a battery container.

FIG. 1 shows a square, plane lid 1 of a sterilizing container which has a laterally downwardly drawn, flange-type lid edge 2. The lid 1 is perforated in a manner not shown in the drawings. The perforated area is covered on the inside by a filter sheet 3. A circular holder 4 is provided with an outer press rim 5 and a central press plate 6 for fixing this filter sheet. Press plate 6 and press rim 5 are joined by radial arms 7. Press plate 6 has a central opening 8 through which a detent pin 9 extends. Detent pin 9 is secured to lid 1 and has a conical tip 10 and a catch groove 11 directly adjoining tip 10.

A disk-shaped locking mechanism 12 is positioned on detent pin 9 protruding from opening 8 of press plate 6. The locking mechanism 12 engages catch groove 11 in a manner which will be explained below and thereby presses holder 4 against the inside of lid 1. To release the locking mechanism 12, it is provided with two actuating members 13 which protrude on opposite sides of locking mechanism 12 from a disk-shaped housing 14 which delimits the locking mechanism.

The structure of locking mechanism 12 will be explained in greater detail below with reference to FIGS. 2 to 4. A guide means 15 with a slideway 16 which leads through the center point and extends over the entire diameter of the circular guide means 15 is located inside the housing 14. Two substantially U-shaped locking members 17 of identical design are mounted in slideway 16 for displacement along slideway 16. The locking member 17 has a bridge 18 which is arranged on one side of slideway 16 and extends parallel to it. Protruding from one of the ends of the bridge is an arm 19 which extends perpendicularly to the bridge 18 and rests at its free end against the bridge 18 of the respective other locking member 17. The arm 19 has a notch 20 on the inside which is designed to semilaterally embrace the detent pin 9 dipping into the housing and to thereby complementarily engage catch groove 11 (FIG. 4).

On the other side, the bridge 18 carries a further arm 21 extending perpendicularly to the bridge 18. The arm 21 extends over the entire width of the slideway 16 and carries at its outer edge the actuating member 13 protruding from the housing.

In this embodiment, the locking member 17 and the actuating member 13 are of integral construction.

A compression spring 24 is supported in recesses 22,23 on the outer side of arm 19 of one locking member 17 and on the inner side of arm 21 of the respective other locking member 17, in each case, and so the two locking members 17 are pushed apart along slideway 16. The inside edges of arms 19 are thereby pressed against each other and so the two arms 19 rest against each other, thereby surrounding the detent pin 9 on all sides, as shown in FIGS. 2 and 4.

By pressing the respective actuating member 13 in the direction of arrow A in FIG. 2, both locking members can be pushed into the interior of housing 14. The arms 19 are thus removed in the region of notches 20 from detent pin 9 and thereby release it (FIG. 3). When the locking members are in this position, the locking mechanism can be removed from the detent pin. Such unlocking is only possible if both actuating members 13 are simultaneously displaced. If only one actuating member 13 is pressed, the associated locking member is disengaged from detent pin 9, but the other locking member remains in its locking position. It is even held particularly reliably in this position by compression spring 24. Hence unlocking is not possible if only one actuating member is actuated. Both actuating members must be actuated simultaneously in order for the locking mechanism to be unlocked The locking mechanism illustrated in FIGS. 1 to 4 can be opened in a simple manner and cleaned. For this purpose, the housing 14 is designed as hood or bell-shaped cover which can be placed over the circular guide means 15. In order to fix housing 14 to guide means 15, the guide means is provided with recesses 25 which extend transversely to the slideway 16 and in which spring-loaded retaining pins 26 are displaceably mounted. When the housing 14 is on the guide means 15, these retaining pins 26 extend through a corresponding opening in the housing. By pressing both retaining pins 26 simultaneously, these can be pushed into the housing which is then removable. When the housing has been removed, the locking members can then be taken out of the slideway or inserted into the slideway from above.

The locking mechanism illustrated in FIGS. 5 and 6 is used in the same way as that shown in FIGS. 1 to 4. This locking mechanism similarly has a disk-shaped housing 30 in which two locking members 32,33 are displaceably mounted on a diametral slideway 31. Each locking member is located on one side of the detent pin 9 of lid 1 extending into housing 30 and is pressed at its front edge against this detent pin 9 by a compression spring 34,35. The compression spring 34,35 is supported in a recess 36,37 of the locking member, and the other end rests on a retaining pin 38,39 which, in turn, engages a recess 40,41 in the housing 30.

In the region of the front edge, each locking member is provided with a notch 42 and 43, respectively, designed in the same way as notches 20 in the embodiment of FIGS. 1 to 4. At the sides, the front edges of the locking members 32 and 33 merge into wedge surfaces 44,45 and 46,47, respectively, which are inclined at 45 degrees to the direction of displacement and are so arranged that when the locking members rest against each other, indentations which are wedgeshaped towards both sides are formed between the contiguous locking members.

In the embodiments shown in FIGS. 5 and 6, the two parts of slideway 31 are laterally slightly offset with respect to each other on opposite sides of detent pin 9 and, therefore, the locking members 32 and 33 guided therein are also slightly offset with respect to each other. The wedge surfaces 44 to 47 are so designed that in spite of this lateral offset of the locking members, the wedge surfaces strike one another at the point at which they merge into the front edges of the locking members. Each locking member thereby has a long and a short wedge surface, as clearly shown in FIG. 5.

Two further guideways 48 and 49 pointing towards the detent pin 9 are arranged transversely to the slideway 31. Two actuating members 50,51 are displaceably mounted in these guideways 48 and 49. At their end facing detent pin 9, the actuating members 50,51 have wedge surfaces 52,53 and 54,55, respectively, which are inclined at 45 degrees to the direction of displacement and extend towards one another. The wedge surfaces merge into a front edge 56 and 57, respectively, extending transversely to the direction of displacement. Both actuating members are of symmetrical design with respect to their longitudinal direction. The guideways 48 and 49 are flush with each other.

In the closed state shown in FIG. 5, locking members 32 and 33 are pressed by compression springs 34 and 35 against detent pin 9 and enclose it completely. The locking mechanism is thereby locked by engagement in the catch groove 11 of detent pin 9. In this case, the actuating members 50 and 51 lie with their wedge surfaces 53 and 54, respectively, against the wedge surfaces 47 and 45, respectively, of the locking members and are pushed into the outer position. In this outer position, the front edge 56 and 57 of the actuating members 50 and 51, respectively, is, however, slightly spaced from the respective other locking member 33 and 32, respectively, as the locking members are likewise laterally offset owing to the lateral offset of the slideway 31 (FIG. 5). There is, therefore, no reciprocal action between the wedge surfaces 52 and 44 or 55 and 46 in this closed position.

If only one of the two actuating members 50 or 51 is pressed in the direction of arrow B in FIG. 5, it is displaced in the direction towards the detent pin 9, and the associated locking member whose wedge surface rests against the wedge surface of the actuating member is displaced against the action of compression spring 34 or 35. The other locking member does, however, remain in its closed position and, therefore, after only a short displacement distance, the displaced actuating member strikes with its front edge 56 or 57 against the side edge of this locking member which has not been displaced. Further displacement of the actuating member and hence also of the associated locking member is thereby prevented.

If, however, both actuating members 50 and 51 are simultaneously pressed in the direction of arrow B in FIG. 5, each actuating member then pushes the associated locking member away from detent pin 9, whereby obstruction of inward motion of the actuating member by the respective other locking member is eliminated. When the actuating members 50 and 51 are pushed in further, wedge surfaces 52 and 55 of the actuating members 50 and 51, respectively, come to rest against the corresponding wedge surfaces 44 and 46, respectively, of the two locking members and, therefore, after the last above-mentioned wedge surfaces have come into contact with one another, the actuating members can now also push the respective other locking member outwardly until the locking members release detent pin 9 in the manner shown in FIG. 6. The locking mechanism is then unlocked.

Accordingly, the fundamental feature of the embodiment shown in FIGS. 5 and 6 is that an actuating member can only be advanced as far as its unlocking position if the other actuating member is also simultaneously actuated. Otherwise, the displacement motion is already blocked after a short distance which is insufficient to release the lock. Hence, in this embodiment, if only one actuating member is actuated, both locking members remain in their closed position.

In the embodiment of FIGS. 7 and 8, the locking mechanism forms, as a whole, the lid 60 of a container 61, for example, a container for accommodating electric batteries.

The lid 60 has a housing of oval configuration but otherwise similar design to the housing 30 of the embodiment of a locking mechanism shown in FIGS. 5 and 6. This housing 62 also has a central slideway 63 extending along the longitudinal axis, with two locking members 64 and 65 mounted for longitudinal displacement therein. The two locking members are pushed into the position remote from each other by a compression spring 66 supported between them At the opposite end, the locking members have claws 67 which protrude laterally from the housing 62 and engage a corresponding recess 68 in the container 61 when the lid is on the container. The lid is thereby locked on the container (FIG. 7). There is, therefore, no central detent pin 9 for locking purposes in this embodiment, the locking being effected on the outside of the housing 62 by the outwardly protruding claws 67.

In the central part of housing 62, one actuating member 71 and 72, respectively, is displaceably mounted in each of the guideways 69 and 70 extending transversely to the slideway 63. These actuating members 71 and 72 protrude laterally from the housing 62.

As in the embodiment of FIGS. 5 and 6, both locking members 64 and 65 and both actuating members 71 and 72 each have two wedge surfaces 73 to 76 and 77 to 80 inclined at 45 degrees to their direction of displacement but, in contrast with the embodiment of FIGS. 5 and 6, these do not move towards one another in wedge-shaped configuration, but move away from one another in wedge-shaped configuration towards the end of the locking members and actuating members, respectively. This reversed inclination of the wedge surfaces results from the reversed direction of motion of the locking members from the closed to the open position. Locking members and actuating members are displaceable in pairs along the same axis, i.e., in this embodiment are not laterally offset with respect to one another. On the other hand, the wedge surfaces 77, 78 and 79,80, respectively, of the two actuating members which all merge into a front edge extending transversely to the direction of displacement are of different length. Therefore, in the closed position shown in FIG. 8, only one of the two wedge surfaces 77,78 and 79,80, respectively, of the actuating members rests against a corresponding wedge surface 73 and 75, respectively, of the associated locking member, while the other wedge surface 78 and 79, respectively, ends at a distance from the respective other locking member (FIG. 8). As in the example of FIGS. 5 and 6, this results in the actuating members first displacing only one locking member when they are pushed in and in then being prevented from further displacement by striking the other locking member if the other locking member is not also displaced from the very beginning, i.e., in this case, too, if only one actuating member is actuated, the motion of the actuating member is blocked and so unlocking is only possible if both actuating members are simultaneously actuated. The locking principle in the embodiment of FIGS. 5 and 6, on the one hand, and FIGS. 7 and 8, on the other hand, is identical, only the directions of inclination of the wedge surfaces being different on account of the different direction of motion of the locking member. The fundamental feature of this development is that in the closed state, only one wedge surface of the actuating member rests against the corresponding wedge surface of the associated locking member, in each case, while the other wedge surface is spaced from the wedge surface of the other locking member and, therefore, when the actuating member is actuated, first only the associated locking member can be displaced. This can be achieved by laterally offset arrangement of the locking members, as in the embodiment of FIGS. 5 and 6, or by the wedge surfaces being of different length, as in the embodiment of FIGS. 7 and 8.

A further improvement in the locking is attained by the actuating members 71,72 also having claws 81 and 82, respectively, which, in turn, engage behind projections on the container so long as the actuating members 71 and 72 are not pushed in. When the actuating members 71 and 72 are pushed in, the claws 81 and 82, respectively, are released and the lid can then be removed from the container. In this way, reliable locking of the lid in the closed state is achieved at four points located at 90 degrees to each other along the circumference.

The locking mechanisms described with reference to FIGS. 1 to 6 are suitable for locking at a central detent pin, whereas the mechanism described with reference to FIGS. 7 and 8 is suitable for external locking at an externally located recess. However, it is, of course, possible to employ the actuating members for both internal and external locking, and those skilled in the-art will then be readily able to effect the necessary reversals in the directions of motion and the corresponding changes in the construction.

What is claimed is:

1. A locking mechanism, in particular, for fixing filter holders on sterilizing containers, comprising:
   a housing in which a locking member is displaceable between two end positions, said locking member engaging behind a locking projection in the first end position and releasing it in the second end position,
   a spring means which biases said locking member in the direction towards said first end position, and
   an actuating member which can be pushed into said housing in order to displace said locking member, characterized in that:
   a second actuating member (13; 50, 51; 71, 72) which can be pushed into said housing is provided, and in that:
   said actuating members (13; 50, 51; 71, 72) protrude from said housing (14; 30; 62) on opposite sides thereof and are actuatable by displacement in the direction towards the respective other actuating member, said locking mechanism (12) only being unlockable if both actuating members are actuated 2. A mechanism as defined in claim 1,
   characterized in that:
   two locking members (17; 32, 33; 64, 65) are mounted in said housing (14; 30; 62),
   and in that:
   one of said two actuating members (13; 50, 51; 71, 72) is associated with each locking member (17; 32, 33; 64, 65).

3. A mechanism as defined in claim 2,
   characterized in that:
   said actuating members (13) are connected to said locking members (17) or said actuating members

(13) and said locking members (17) are of integral construction.

4. A mechanism as defined in claim 3, characterized in that:
said locking members (17) have an arm (19) which extends transversely to the direction of displacement and engages behind a detent pin (9) in said housing (14) when said locking member (17) is in said first end position,
and in that:
in said first end position, said arms (19) of said two locking members (17) rest against each other, thereby enclosing said detent pin (9).

5. A mechanism as defined in claim 4, characterized in that:
a spring (24) is arranged between said arm (19) of one locking member (17) and said other locking member (17) to push both locking members (17) into said first end position 6. A mechanism as defined in claim 5, characterized in that:
said two locking members (17) are of identical construction and are inserted into said housing (14) in point-symmetrical relation to said detent pin (9).

7. A mechanism as defined in claim 2, characterized in that:
the respective other locking member (33, 32; 65, 64) moves into the path of displacement of the actuating member (51, 50; 72, 71) associated with the one locking member (32, 33; 64, 65) and thereby prevents its displacement so long as the respective other locking member (33, 32; 65, 64) is in said first end position,
and in that:
prior to obstruction by the respective other locking member (33, 32; 65, 64), each actuating member (51, 50; 72, 71) can be pushed forward so far that the associated locking member (32, 33; 64, 65) is removed from the path of displacement of the respective other actuating member (50, 51; 71, 72).

8. A mechanism as defined in claim 7, characterized in that:
said actuating members (32, 33; 71, 72) are displaceable perpendicularly to said locking members (50, 51; 64, 65) in said housing (30; 62), said actuating members (50, 51; 71, 72) and said locking members (32, 33; 64, 65) being, in each case, arranged opposite each other.

9. A mechanism as defined in claim 8, characterized in that:
said actuating members (50, 51; 71, 72) and said associated locking members (33, 32; 65, 64) have contiguous wedge surfaces (53, 47, 54, 45; 73, 77, 80, 75) for transmitting the displacement motion from said actuating members to said locking members.

10. A mechanism as defined in claim 9, characterized in that:
said actuating members (50, 51; 71, 72) and said locking members (32, 33; 64, 65) not associated therewith have additional wedge surfaces (52, 44, 55, 46; 78, 76, 74, 79),
and in that:
the additional wedge surface of an actuating member rests against the additional wedge surface of the locking member when said actuating member is displaced.

11. A mechanism as defined in one of claim 7, characterized in that:
said locking mechanism is designed as cover (60) of a container (61), in particular, a battery container, and said container (61) is provided with the locking projections (68).

12. A mechanism as defined in claim 11, characterized in that:
said actuating members (71, 72) have claws (81, 82) which engage behind projections on said container (61) when said actuating members (71, 72) are not pushed in and release these projections when said actuating members are pushed in.

13. A mechanism as defined in claim 8, characterized in that:
said locking mechanism is designed as cover (60) of a container (61), in particular, a battery container, and said container (61) is provided with the locking projections (68).

14. A mechanism as defined in claim 9, characterized in that:
said locking mechanism is designed as cover (60) of a container (61), in particular, a battery container, and said container (61) is provided with the locking projections (68).

15. A mechanism as defined in claim 10, characterized in that:
said locking mechanism is designed as cover (60) of a container (61), in particular, a battery container, and said container (61) is provided with the locking projections (68).

* * * * *